(12) United States Patent
Kaur et al.

(10) Patent No.: US 9,696,629 B2
(45) Date of Patent: Jul. 4, 2017

(54) PHOTORESIST PATTERN TRIMMING COMPOSITIONS AND METHODS

(71) Applicant: Rohm and Haas Electronic Materials LLC, Marlborough, MA (US)

(72) Inventors: Irvinder Kaur, Northborough, MA (US); Cong Liu, Shrewsbury, MA (US); Kevin Rowell, Brighton, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 14/971,087

(22) Filed: Dec. 16, 2015

(65) Prior Publication Data

US 2016/0187783 A1    Jun. 30, 2016

Related U.S. Application Data

(60) Provisional application No. 62/099,095, filed on Dec. 31, 2014.

(51) Int. Cl.
*G03F 7/11* (2006.01)
*G03F 7/42* (2006.01)
(Continued)

(52) U.S. Cl.
CPC ............. *G03F 7/42* (2013.01); *C07C 309/01* (2013.01); *C07C 309/28* (2013.01); *C07C 309/33* (2013.01); *C07C 309/39* (2013.01); *C07C 309/40* (2013.01); *G03F 7/004* (2013.01); *G03F 7/0397* (2013.01); *G03F 7/2041* (2013.01); *G03F 7/38* (2013.01); *G03F 7/405* (2013.01)

(58) Field of Classification Search
CPC ... G03F 7/004; G03F 7/11; G03F 7/32; G03F 7/40; G03F 7/20; G03F 7/0397; G03F 7/2022; G03F 7/38; C07C 309/01; C07C 309/28; C07C 309/33; C07C 309/39; C07C 309/40
USPC ...... 430/270.1, 271.1, 273.1, 322, 325, 329, 430/330, 913; 560/9; 562/30
See application file for complete search history.

(56) References Cited

U.S. PATENT DOCUMENTS 6,180,320 B1  1/2001 Saito et al.
6,492,075 B1  12/2002 Templeton et al.
(Continued)

FOREIGN PATENT DOCUMENTS

CN   1531018 A   9/2004
JP   2002006512 A   1/2002
(Continued)

OTHER PUBLICATIONS

U.S. Co-pending U.S. Appl. No. 15/297,545, filed Oct. 19, 2016.
(Continued)

*Primary Examiner* — Amanda C Walke
(74) *Attorney, Agent, or Firm* — Jonathan D. Baskin

(57) ABSTRACT

Photoresist pattern trimming compositions are provided. The compositions comprise: a matrix polymer, an aromatic sulfonic acid and a solvent, wherein the aromatic sulfonic acid comprises one or more fluorinated alcohol group. Also provided are methods of trimming a photoresist pattern using the trimming compositions. The compositions and methods find particular applicability in the manufacture of semiconductor devices.

21 Claims, 1 Drawing Sheet

(51) Int. Cl.

| | | |
|---|---|---|
| G03F 7/004 | (2006.01) | |
| C07C 309/01 | (2006.01) | |
| C07C 309/28 | (2006.01) | |
| C07C 309/33 | (2006.01) | |
| C07C 309/39 | (2006.01) | |
| C07C 309/40 | (2006.01) | |
| G03F 7/039 | (2006.01) | |
| G03F 7/38 | (2006.01) | |
| G03F 7/20 | (2006.01) | |
| G03F 7/40 | (2006.01) | |

(56) References Cited

U.S. PATENT DOCUMENTS

| 7,338,750 | B2 | 3/2008 | Kozawa et al. | |
|---|---|---|---|---|
| 2003/0017711 | A1 | 1/2003 | Mahorowala et al. | |
| 2003/0138736 | A1* | 7/2003 | Nitta | G03F 7/38 |
| | | | | 430/326 |
| 2009/0311490 | A1 | 12/2009 | Burns et al. | |
| 2013/0171574 | A1 | 7/2013 | Xu | |
| 2013/0171825 | A1* | 7/2013 | Xu | H01L 21/0274 |
| | | | | 438/694 |
| 2014/0186772 | A1* | 7/2014 | Pohlers | G03F 7/405 |
| | | | | 430/311 |
| 2015/0185620 | A1* | 7/2015 | Liu | G03F 7/405 |
| | | | | 430/319 |

FOREIGN PATENT DOCUMENTS

| JP | 2002299202 A | | 10/2002 |
|---|---|---|---|
| JP | 2003277347 A | * | 10/2003 |
| JP | 04329216 B2 | | 9/2009 |
| JP | 2013218191 A | | 10/2013 |

OTHER PUBLICATIONS

U.S. Co-pending U.S. Appl. No. 15/297,556, filed Oct. 19, 2016.
Search report for corresponding Taiwan Application No. 104141987 dated Nov. 22, 2016.

* cited by examiner

PHOTORESIST PATTERN TRIMMING COMPOSITIONS AND METHODS

This application claims the benefit of priority under 35 U.S.C. §119(e) to U.S. Provisional Application No. 62/099,095, filed Dec. 31, 2014, the entire contents of which are incorporated herein by reference.

BACKGROUND

The invention relates generally to the manufacture of electronic devices. More specifically, this invention relates to compositions and methods for trimming photoresist patterns useful in shrink processes for the formation of fine lithographic patterns.

In the semiconductor manufacturing industry, photoresist materials are used for transferring an image to one or more underlying layers, such as metal, semiconductor and dielectric layers, disposed on a semiconductor substrate, as well as to the substrate itself. Photoresist materials further find use, for example, in semiconductor manufacture in the formation of ion implantation masks. To increase the integration density of semiconductor devices and allow for the formation of structures having dimensions in the nanometer range, photoresists and photolithography processing tools having high-resolution capabilities have been and continue to be developed.

Positive-tone chemically amplified photoresists are conventionally used for high-resolution processing. Such resists typically employ a resin having acid-labile leaving groups and a photoacid generator. Exposure to actinic radiation causes the acid generator to form an acid which, during post-exposure baking, causes cleavage of the acid-labile groups in the resin. This creates a difference in solubility characteristics between exposed and unexposed regions of the resist in an aqueous alkaline developer solution. In a positive tone development (PTD) process, exposed regions of the resist are soluble in the aqueous alkaline developer and are removed from the substrate surface, whereas unexposed regions, which are insoluble in the developer, remain after development to form a positive image.

Lithographic scaling has conventionally been achieved by increasing the numerical aperture of the optical exposure equipment and use of shorter exposure wavelengths, for example, 200 nm or less, for example, 193 nm or EUV wavelengths (e.g., 13.5 nm), with chemically amplified photoresists. To further improve lithographic performance, immersion lithography tools have been developed to effectively increase the numerical aperture (NA) of the lens of the imaging device, for example, a scanner having a KrF or ArF light source. This is accomplished by use of a relatively high refractive index fluid (i.e., an immersion fluid) between the last surface of the imaging device and the upper surface of the semiconductor wafer. The immersion fluid allows a greater amount of light to be focused into the resist layer than would occur with an air or inert gas medium. When using water as the immersion fluid, the maximum numerical aperture can be increased, for example, from 1.2 to 1.35. With such an increase in numerical aperture, it is possible to achieve a 40 nm half-pitch resolution in a single exposure process, thus allowing for improved design shrink. This standard immersion lithography process, however, is generally not suitable for manufacture of devices requiring greater resolution.

At present, the industry has reached a point at which further increases in numerical aperture or reductions in exposure wavelength have reached a practical limit. As a result, alternative methods of scaling integrated circuit lithography are being investigated. Considerable effort has been made to extend the practical resolution beyond that achieved with standard photolithographic techniques from both a materials and processing standpoint. For example, multiple (i.e., double or higher order) patterning processes have been proposed for printing CDs and pitches beyond lower resolution limits of conventional lithographic tools. One such double patterning process is litho-litho-etch (LLE) double patterning, which involves formation of a first lithographic photoresist pattern followed by formation of a second lithographic photoresist pattern, wherein lines of the second pattern are disposed between adjacent lines of the first pattern. LLE double patterning and other advanced lithographic processes often require the formation of isolated features such as lines or posts by direct lithographic printing. The formation of isolated features with an acceptable process window, however, can pose a challenge as a result of poor aerial image contrast at defocus.

To form finer photoresist patterns than attainable by direct imaging alone, photoresist pattern trimming processes have been proposed. See, e.g., U.S. Patent Application Pub. Nos. US2013/0171574A1 and US2014/0186772A1. Photoresist trimming processes typically involve contacting a photoresist pattern that includes a polymer having acid labile groups with a composition containing an acid or acid generator. The acid or acid generated from the acid generator causes deprotection in a surface region of the resist pattern, which region is then removed, for example, by contact with a developer solution. The features of the resulting resist pattern are therefore reduced in size as compared with the original resist pattern.

The inventors have recognized the desirability of reducing resist pattern dimensions, while providing good line width roughness (LWR) and/or iso-dense bias properties. There is a continuing need for compositions and methods useful in electronic device fabrication that address one or more problem and/or need in art.

SUMMARY OF THE INVENTION

In accordance with a first aspect of the invention, photoresist pattern trimming compositions are provided. The compositions comprise: a matrix polymer, an aromatic sulfonic acid and a solvent, wherein the aromatic sulfonic acid comprises one or more fluorinated alcohol group.

In accordance with a further aspect of the invention, methods of trimming a photoresist pattern are provided. The methods comprise: (a) providing a semiconductor substrate; (b) forming a photoresist pattern on the substrate, wherein the photoresist pattern is formed from a photoresist composition comprising: a matrix polymer comprising an acid labile group; a photoacid generator; and a solvent; (c) coating a photoresist trimming composition as described herein on the substrate over the photoresist pattern; (d) heating the coated substrate, thereby causing a change in polarity of the photoresist matrix polymer in a surface region of the photoresist pattern; and (e) contacting the photoresist pattern with a rinsing agent to remove the surface region of the photoresist pattern, thereby forming a trimmed photoresist pattern.

The photoresist pattern trimming compositions and methods of the invention can produce fine lithographic patterns, with controllably reduced resist pattern dimensions. Preferred compositions and methods of the invention allow for the formation of patterns having beneficial line width roughness properties and allow for the formation of isolated patterns such as isolated lines and posts with desirable iso-dense bias characteristics.

The terminology used herein is for the purpose of describing particular embodiments only and is not intended to be limiting of the invention. "Alkyl" includes linear, branched and cyclic alkyl. Aromatic groups can be substituted or contain heteroatoms, and include single aromatic rings such as phenyl or pyridyl, tethered rings such as biphenyl, fused aromatic rings such as naphthyl, anthracenyl, pyrenyl, or quinolinyl, and fused ring systems having both aromatic and non-aromatic rings such as 1,2,3,4-tetrahydronaphthalene, 9,10-dihydroanthracene, or fluorene, and their various valency forms. The singular forms "a", "an" and "the" are intended to include the plural forms as well, unless the context clearly indicates otherwise.

DESCRIPTION OF THE DRAWINGS

The present invention will be described with reference to the following drawing, in which like reference numerals denote like features, and in which.

DETAILED DESCRIPTION

Photoresist Pattern Trimming Compositions

Figure 1A:
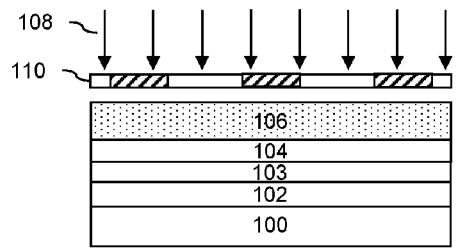
FIG. 1A-H illustrates a process flow for forming a photolithographic pattern in accordance with the invention.

The photoresist pattern trimming compositions include a matrix polymer, an aromatic sulfonic acid that includes one or more fluorinated alcohol group, and a solvent, and can include one or more optional additional components. When coated over a photoresist pattern formed from a chemically amplified photoresist composition, photoresist trimming compositions in accordance with the invention can provide fine lithographic patterns with controllably reduced resist pattern dimensions. Photoresist compositions of the invention can also provide favorable LWR and iso-dense bias properties.

The matrix polymer allows for the compositions to be coated over the photoresist pattern in the form of a layer having a desired thickness. This will help to ensure the presence of a sufficient content of acid for interaction with the photoresist pattern surface.

The matrix polymer should have good solubility in the rinsing solution to be used in the trimming process. For example, the matrix polymer can be soluble in an aqueous alkaline developer, preferably aqueous quaternary ammonium hydroxide solutions such as aqueous tetramethylammonium hydroxide, or in water. To minimize residue defects originated from the overcoat materials, the dissolution rate of a dried layer of the trimming composition should be greater than that of the photoresist pattern surface region to be removed by the developer solution. The matrix polymer typically exhibits a developer dissolution rate of 100 Å/second or higher, preferably 1000 Å/second or higher. The matrix polymer is soluble in the solvent of the trimming composition, described herein. The matrix polymer can be chosen, for example, from polyvinyl alcohols, polyacrylic acids, polyvinyl pyrrolidones, polyvinyl amines, polyvinyl acetals, poly(meth)acrylates and combinations thereof. Preferably, the polymer contains one or more functional group chosen from —OH, —COOH, —SO$_3$H, SiOH, hydroxyl styrene, hydroxyl naphthalene, sulfonamide, hexafluoroisopropyl alcohol, anhydrates, lactones, esters, ethers, allylamine, pyrolidones and combinations thereof.

The content of the matrix polymer in the composition will depend, for example, on the target thickness of the layer, with a higher polymer content being used for thicker layers. The matrix polymer is typically present in the compositions in an amount of from 80 to 99 wt %, more typically from 90 to 98 wt %, based on total solids of the trimming composition. The weight average molecular weight (Mw) of the polymer is typically less than 400,000, preferably from 3000 to 50,000, more preferably from 3000 to 25,000.

Polymers useful in the overcoat compositions can be homopolymers or can be copolymers having a plurality of distinct repeat units, for example, two, three or four distinct repeat units. The trimming compositions typically include a single polymer, but can optionally include one or more additional polymer. Suitable polymers and monomers for use in the overcoat compositions are commercially available and/or can readily be made by persons skilled in the art.

The trimming compositions further include an aromatic acid that includes one or more fluorinated alcohol group. In the case of a photoresist based on deprotection reaction, the acid with heat can cleave the bond of acid labile groups in the photoresist pattern. The aromatic acid is preferably a sulfonic acid comprising a phenyl, biphenyl, naphthyl, anthracenyl, thiophene or furan group. For purposes of tuning lithographic properties and LWR, it has been found that the use of slow diffusing sulfonic acids is preferred. Particularly preferred are sulfonic acids substituted with bulky groups causing the acids to be slow diffusing. Suitable bulky groups include, for example, adamantyl, branched and cyclic optionally substituted alkyl and fluorinated alcohols. The fluorinated alcohol group can be partially or completely fluorinated. Preferred fluorinated alcohol groups include a fluorine atom or a pendant fluorinated group bonded to a carbon at the alpha position of the alcohol hydroxyl. Particularly preferred are hexafluoroalcohol groups. For purposes of increasing the bulkiness of the aromatic acid, it is preferred that the aromatic acid include a plurality of fluorinated alcohol or other groups. It is also preferred that the fluoroalcohol group is bonded to an aromatic ring of the aromatic sulfonic acid through a linking group. Suitable linking groups include, for example, sulfur, optionally substituted amino groups, amides, ethers, carbonyl esters, sulfonyl esters, sulfones, sulfonamides and divalent hydrocarbon group, for example, C1-20 straight chain, branched or cyclic optionally substituted hydrocarbon groups, and combinations thereof.

The aromatic sulfonic acid is preferably chosen from acids of the following general formula (I):

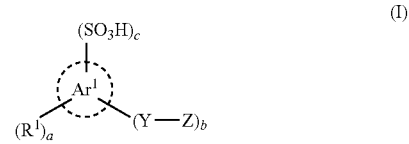

Ar$^1$ represents an aromatic group, which may be carbocyclic, heterocyclic, or a combination thereof. The aromatic group may include a single aromatic ring such as phenyl or pyridyl; fused aromatic rings such as naphthyl, anthracenyl, pyrenyl, or quinolinyl; or fused ring systems having both aromatic and non-aromatic rings such as 1,2,3,4-tetrahydronaphthalene, 9,10-dihydroanthracene, or fluorene. Optionally, the aromatic group may be substituted. As used herein, the term "substituted" alkyl or aromatic group refers to any such group having one or more of its hydrogens replaced with one or more substituents selected from C$_{1-30}$ alkyl, C$_{2-30}$ alkenyl, C$_{7-30}$ aralkyl, C$_{6-30}$ aryl, —OR, —C$_{1-30}$ alkylene-OR, and —C$_{1-30}$ alkylidene-OR; wherein R is selected from H, C$_{1-30}$ alkyl, C$_{2-30}$ alkenyl, and C$_{6-30}$ aryl. A wide variety of aromatic groups may be used for Ar$^1$, which may be unsubstituted or substituted. Such unsubstituted aromatic groups have from 5 to 40 carbons, preferably from 6 to 35 carbons, and more preferably from 6 to 30 carbons. Suitable aromatic groups include, but are not limited to: phenyl, biphenyl, naphthalenyl, anthracenyl, phenanthrenyl, pyrenyl, tetracenyl, triphenylenyl, tetraphenyl, benzo[f]tetraphenyl, benzo[m]tetraphenyl, benzo[k]tetraphenyl, pentacenyl, perylenyl, benzo[a]pyrenyl, benzo[e]pyrenyl, benzo[ghi]perylenyl, coronenyl, quinolonyl, 7,8-benzoquinolinyl, fluorenyl, and 12H-dibenzo[b,h]fluorenyl, each of which may by unsubstituted or substituted. R$^1$ independently represents a group chosen from carboxyl, hydroxy, nitro, cyano, C1-5 alkoxy and formyl. Y independently represents a linking group chosen, for example, from sulfur, optionally substituted amino groups, amides, ethers, carbonyl esters, sulfonyl esters, sulfones, sulfonamides and divalent hydrocarbon group, for example, C1-20 straight chain, branched or cyclic optionally substituted hydrocarbon groups, and combinations thereof.

Z independently represents a group chosen from fluorinated alcohols, fluorinated esters, substituted or unsubstituted alkyl, C5 or higher monocyclic, polycyclic, fused polycyclic cycloaliphatic, or aryl, which may optionally comprise a heteroatom, provided at least one occurrence of Z is a fluorinated alcohol group. a is an integer of 0 or greater, typically 0 to 2; b is an integer of 1 or greater, typically 1 or 2; and c is an integer of 1 or greater, typically 1 to 2, provided that a+b+c is at least 2 and not greater than the total number of available aromatic carbon atoms of the aromatic group. Typically, a+b+c is from 2 to 5, more typically 2 or 3, Exemplary aromatic sulfonic acids for use in the pattern trimming compositions include, without limitation, the following:

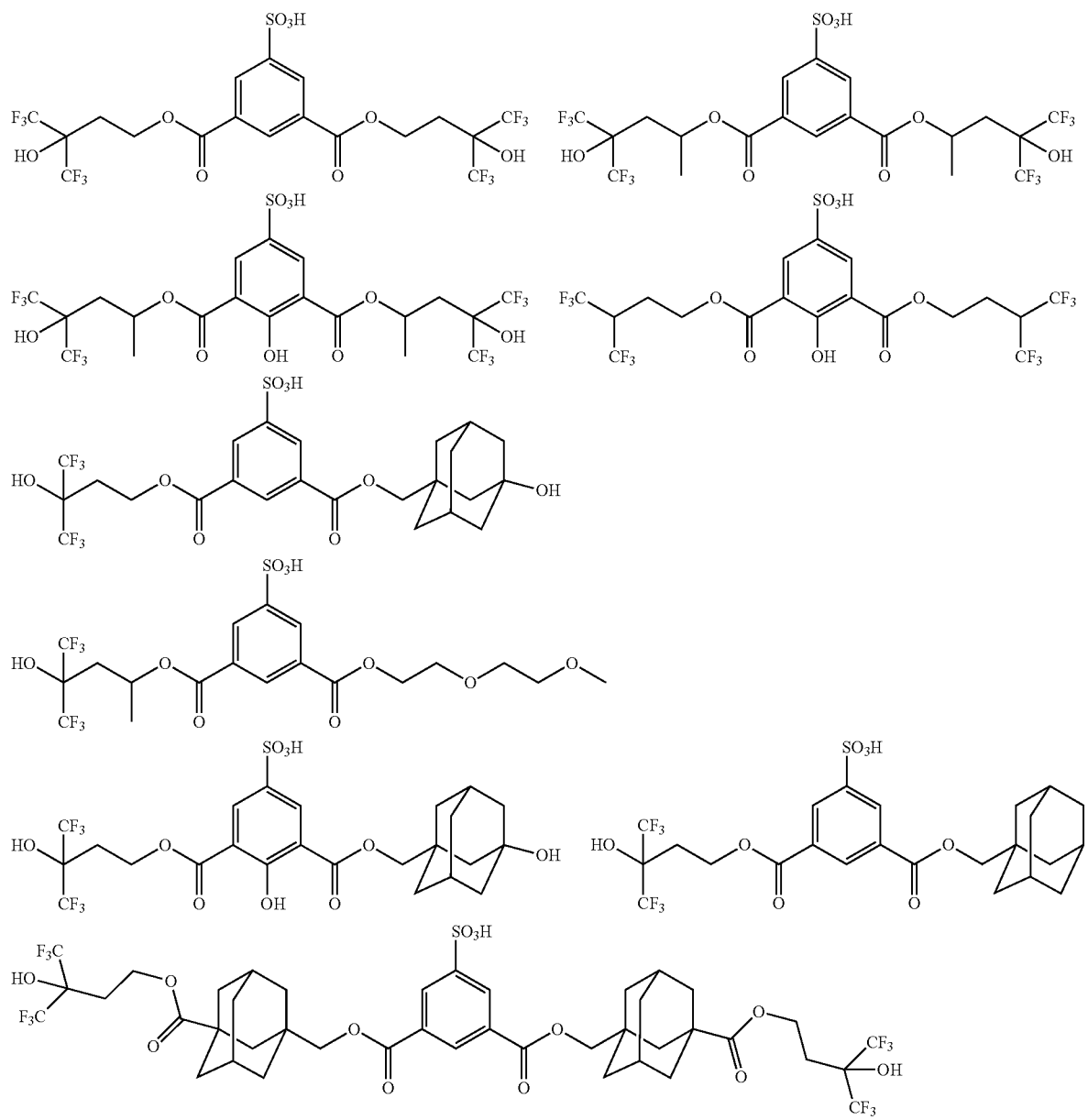

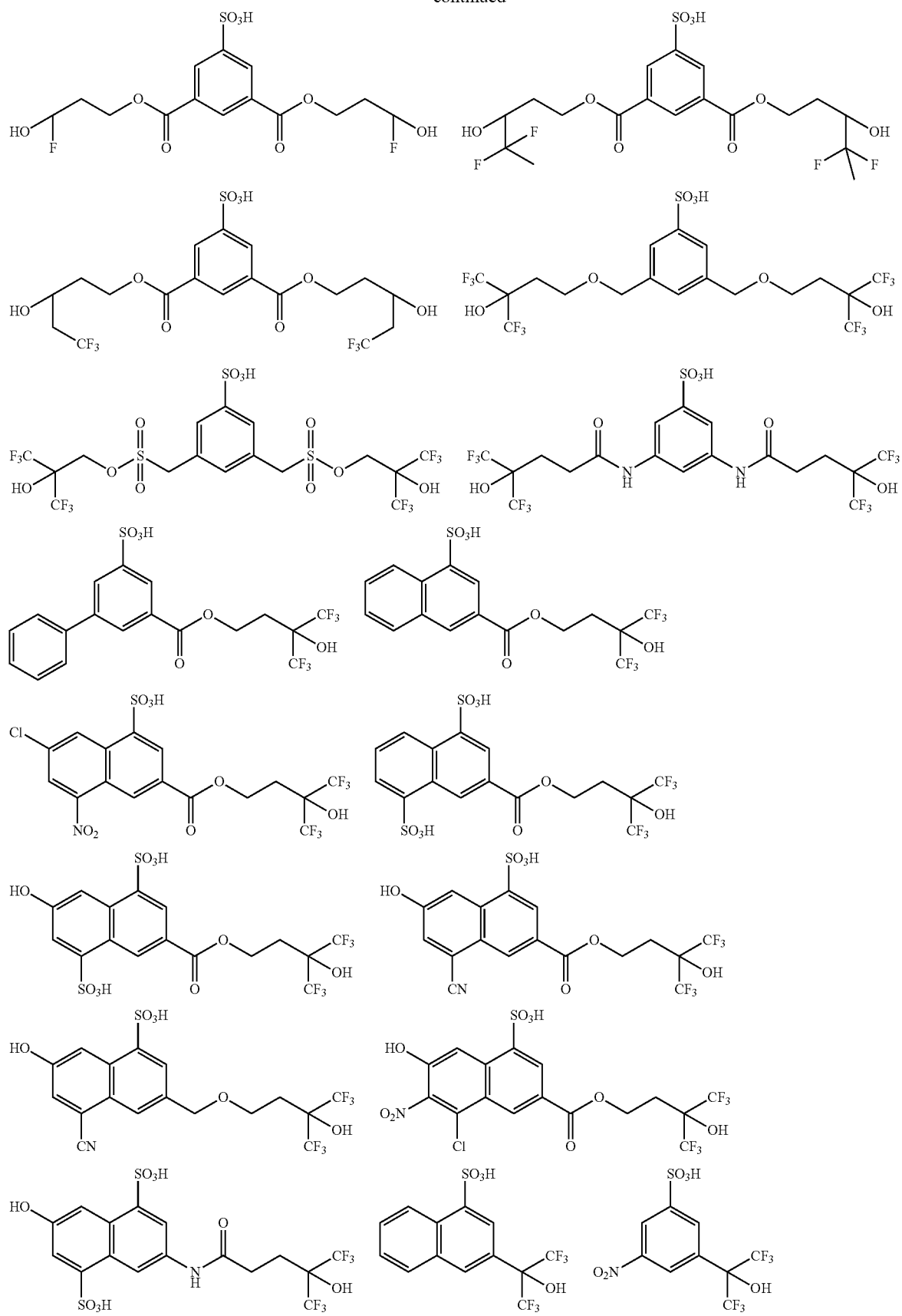

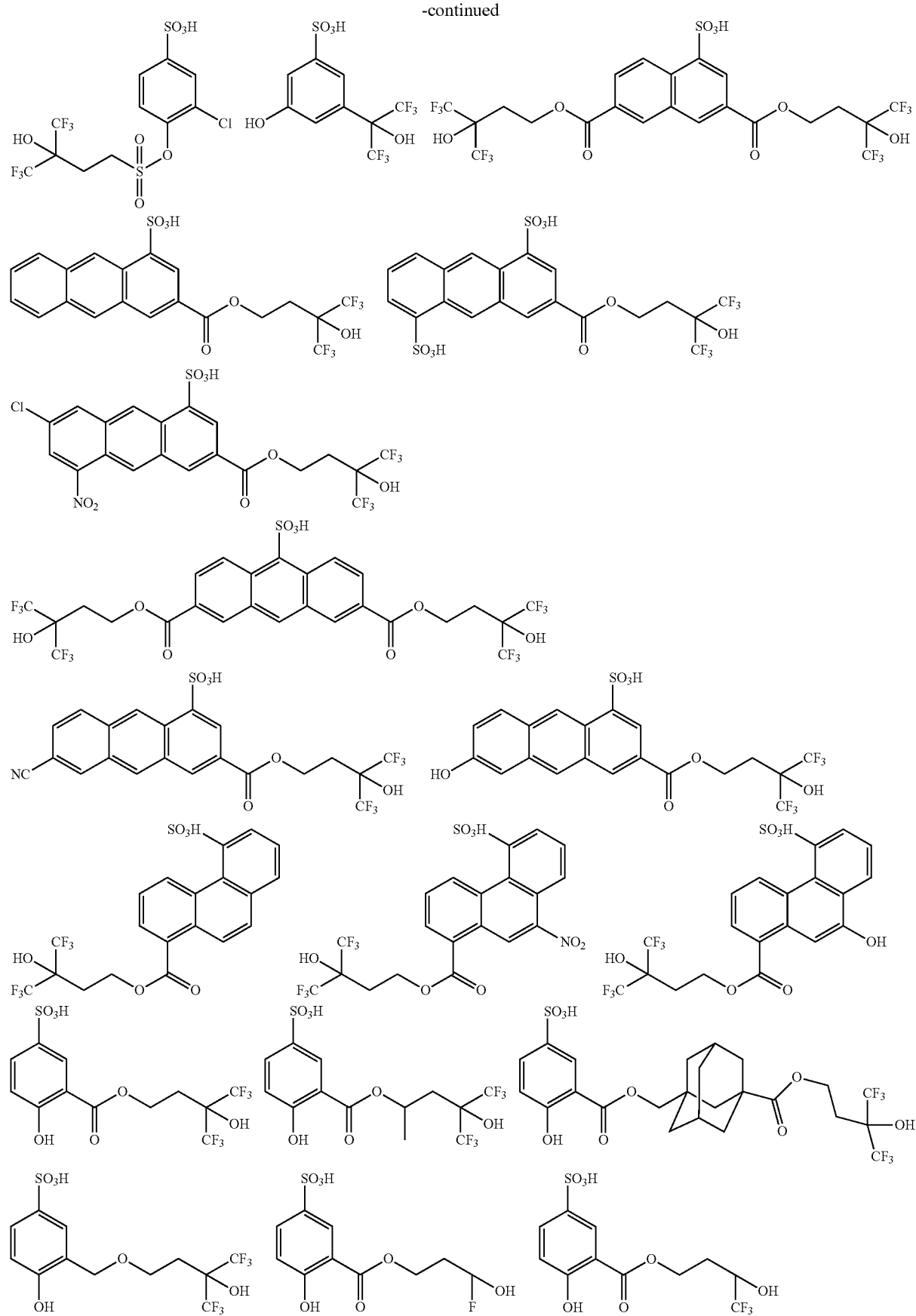

11 12
-continued
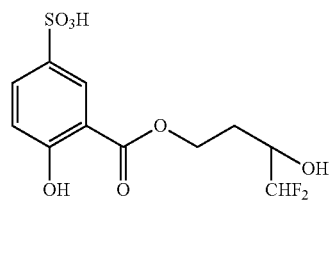 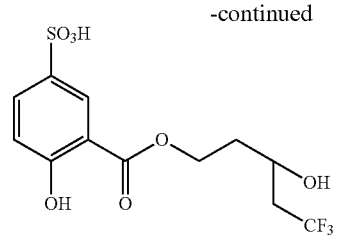 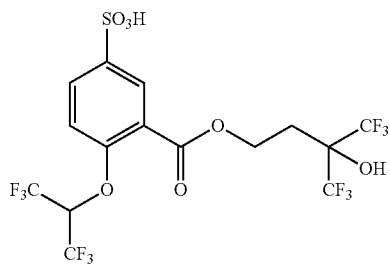
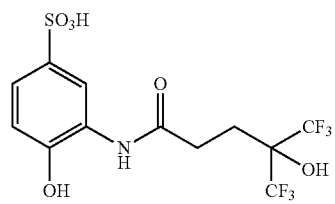 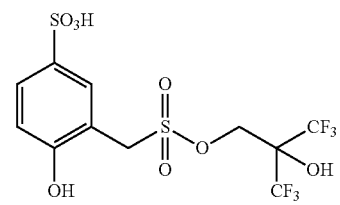 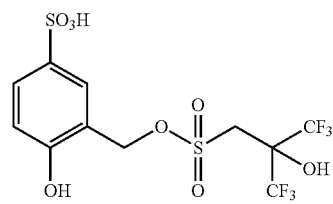
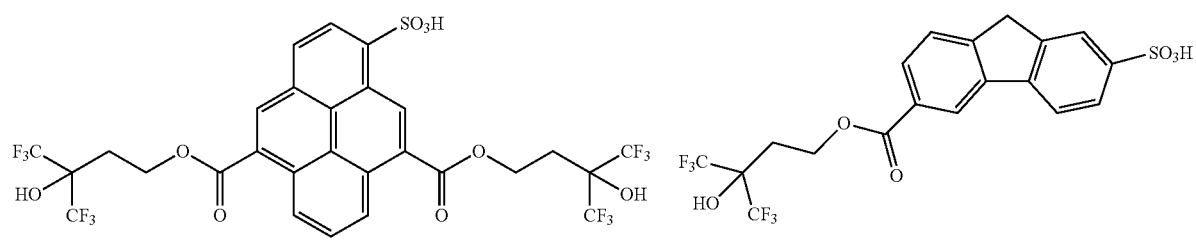
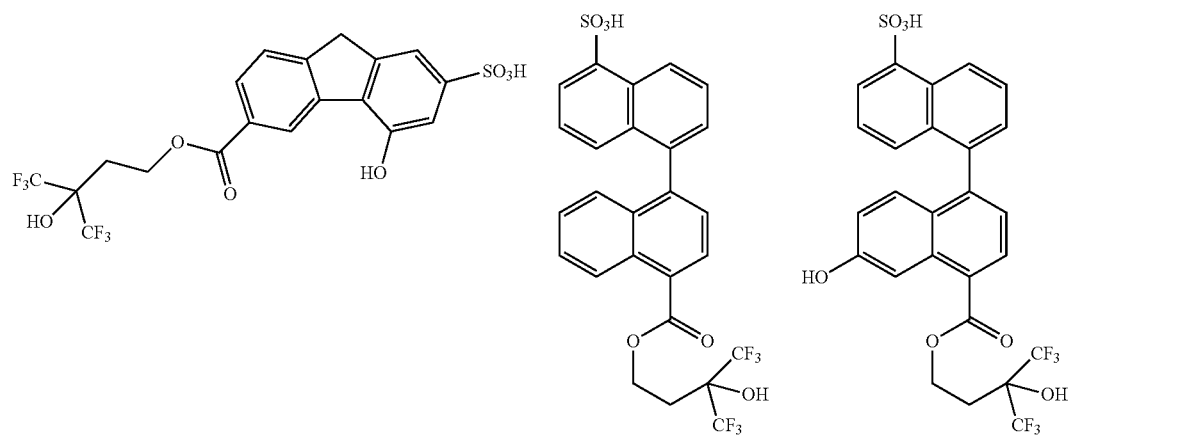
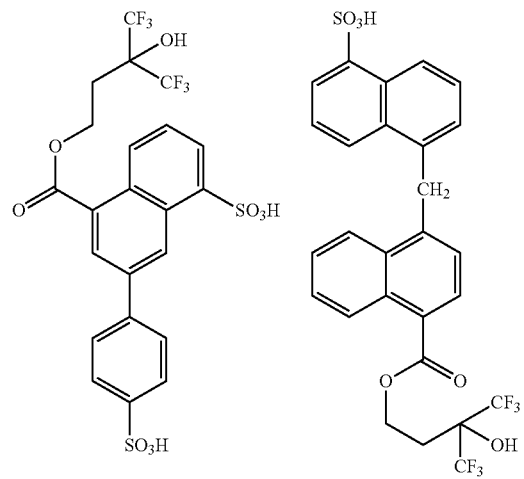

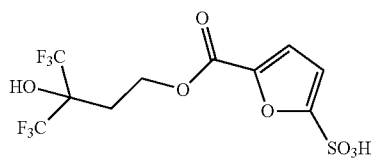

The aromatic acid is typically present in the compositions in an amount of from 0.01 to 20 wt %, more typically from 0.1 to 10 wt % or from 1 to 5 wt %, based on total solids of the trimming composition. Suitable aromatic acids are commercially available or can be readily made by persons skilled in the art.

The trimming compositions further include a solvent or solvent mixture. The trimming compositions can take the form of an aqueous solution. Suitable solvent materials to formulate and cast the trimming compositions exhibit very good solubility characteristics with respect to the non-solvent components of the trimming composition, but do not appreciably dissolve the underlying photoresist pattern so as to minimize intermixing. The solvent is typically chosen from water, organic solvents and mixtures thereof. Suitable organic solvents for the trimming composition include, for example: alkyl esters such as alkyl propionates such as n-butyl propionate, n-pentyl propionate, n-hexyl propionate and n-heptyl propionate, and alkyl butyrates such as n-butyl butyrate, isobutyl butyrate and isobutyl isobutyrate; ketones such as 2,5-dimethyl-4-hexanone and 2,6-dimethyl-4-heptanone; aliphatic hydrocarbons such as n-heptane, n-nonane, n-octane, n-decane, 2-methylheptane, 3-methylheptane, 3,3-dimethylhexane and 2,3,4-trimethylpentane, and fluorinated aliphatic hydrocarbons such as perfluoroheptane; alcohols such as straight, branched or cyclic $C_4$-$C_9$ monohydric alcohol such as 1-butanol, 2-butanol, isobutyl alcohol, tert-butyl alcohol, 3-methyl-1-butanol, 1-pentanol, 2-pentanol, 4-methyl-2-pentanol, 1-hexanol, 1-heptanol, 1-octanol, 2-hexanol, 2-heptanol, 2-octanol, 3-hexanol, 3-heptanol, 3-octanol and 4-octanol; 2,2,3,3,4,4-hexafluoro-1-butanol, 2,2,3,3,4,4,5,5-octafluoro-1-pentanol and 2,2,3,3,4,4,5,5,6,6-decafluoro-1-hexanol, and $C_5$-$C_9$ fluorinated diols such as 2,2,3,3,4,4-hexafluoro-1,5-pentanediol, 2,2,3,3,4,4,5,5-octafluoro-1,6-hexanediol and 2,2,3,3,4,4,5,5,6,6,7,7-dodecafluoro-1,8-octanediol; ethers such as isopentyl ether and dipropylene glycol monomethyl ether; and mixtures containing one or more of these solvents. Of these organic solvents, alcohols, aliphatic hydrocarbons and ethers are preferred. The solvent component of the trimming composition is typically present in an amount of from 90 to 99 wt % based on the trimming composition.

The trimming compositions may include optional additives. For example, the trimming compositions can include an additional component that reacts with surface region of the resist pattern, rendering the surface region soluble in an organic solvent rinsing agent. This optional component preferably contains functional groups chosen from —OH, —NH—, —SH, ketones, aldehydes, —SiX wherein X is a halogen, vinyl ethers and combinations thereof. Without wishing to be bound by any particular theory, it is believed that the component diffuses into the resist pattern and reacts with carboxylic acid groups of the pattern. This reaction results in a polarity change of the surface, rendering the surface soluble in the organic solvent. This component can be useful, for example, where the photoresist pattern is formed by negative tone development (NTD) wherein the pattern is composed of exposed portions of the photoresist comprising acid-labile groups. Such component if used is typically present in an amount of from 0.1 to 10 wt % based on total solids of the trimming composition.

The trimming composition can further include a surfactant. Typical surfactants include those which exhibit an amphiphilic nature, meaning that they can be both hydrophilic and hydrophobic at the same time. Amphiphilic surfactants possess a hydrophilic head group or groups, which have a strong affinity for water and a long hydrophobic tail, which is organophilic and repels water. Suitable surfactants can be ionic (i.e., anionic, cationic) or nonionic. Further examples of surfactants include silicone surfactants, poly (alkylene oxide) surfactants, and fluorochemical surfactants. Suitable non-ionic surfactants include, but are not limited to, octyl and nonyl phenol ethoxylates such as TRITON® X-114, X-100, X-45, X-15 and branched secondary alcohol ethoxylates such as TERGITOL™ TMN-6 (The Dow Chemical Company, Midland, Mich. USA). Still further exemplary surfactants include alcohol (primary and secondary) ethoxylates, amine ethoxylates, glucosides, glucamine, polyethylene glycols, poly(ethylene glycol-co-propylene glycol), or other surfactants disclosed in *McCutcheon's Emulsifiers and Detergents*, North American Edition for the Year 2000 published by Manufacturers Confectioners Publishing Co. of Glen Rock, N.J. Nonionic surfactants that are acetylenic diol derivatives also can be suitable. Such surfactants are commercially available from Air Products and Chemicals, Inc. of Allentown, Pa. and sold under the trade names of SURFYNOL® and DYNOL®. Additional suitable surfactants include other polymeric compounds such as the tri-block EO-PO-EO co-polymers PLURONIC® 25R2, L121, L123, L31, L81, L101 and P123 (BASF, Inc.). Such surfactant and other optional additives if used are typically present in the composition in minor amounts such as from 0.01 to 10 wt % based on total solids of the trimming composition.

The trimming compositions are preferably free of cross-linking agents as such materials can result in a dimensional increase of the resist pattern.

The trimming compositions can be prepared following known procedures. For example, the compositions can be prepared by dissolving solid components of the composition in the solvent components. The desired total solids content of the compositions will depend on factors such as the desired final layer thickness. Preferably, the solids content of the trimming compositions is from 1 to 10 wt %, more preferably from 1 to 5 wt %, based on the total weight of the composition.

Photoresist Pattern Trimming Methods

Processes in accordance with the invention will now be described with reference to FIG. 1A-H, which illustrates an exemplary process flow for forming a photolithographic pattern using a photoresist pattern trimming technique in accordance with the invention. While the illustrated process flow is of a positive tone development process, the invention is also applicable to negative tone development (NTD)

processes. Also, while the illustrated process flow describes a patterning process in which a single resist mask is used to transfer the trimmed photoresist pattern to the underlying substrate, it should be clear that the trimming method can be used in other lithographic processes, for example, in double patterning processes such as litho-litho-etch (LLE), litho-etch-litho-etch (LELE) or self-aligned double patterning (SADP), as an ion implantation mask, or any other lithographic process where trimming of a photoresist pattern would be beneficial.

FIG. 1A depicts in cross-section a substrate 100 which may include various layers and features. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned 102 may be provided over the substrate 100. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layers to be etched 102 will vary depending on the materials and particular devices being formed.

Depending on the particular layers to be etched, film thicknesses and photolithographic materials and process to be used, it may be desired to dispose over the layers 102 a hard mask layer 103 and/or a bottom antireflective coating (BARC) 104 over which a photoresist layer 106 is to be coated. Use of a hard mask layer may be desired, for example, with very thin resist layers, where the layers to be etched require a significant etching depth, and/or where the particular etchant has poor resist selectivity. Where a hard mask layer is used, the resist patterns to be formed can be transferred to the hard mask layer 103 which, in turn, can be used as a mask for etching the underlying layers 102. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer can include a single layer or a plurality of layers of different materials. The hard mask layer can be formed, for example, by chemical or physical vapor deposition techniques.

A bottom antireflective coating may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist layer 106 formed from a chemically amplified photosensitive composition comprising a matrix polymer having acid labile groups is disposed on the substrate over the antireflective layer (if present). The photoresist composition can be applied to the substrate by spin-coating, dipping, roller-coating or other conventional coating technique. Of these, spin-coating is typical. For spin-coating, the solids content of the coating solution can be adjusted to provide a desired film thickness based upon the specific coating equipment utilized, the viscosity of the solution, the speed of the coating tool and the amount of time allowed for spinning. A typical thickness for the photoresist layer 106 is from about 500 to 3000 Å.

The layer 106 can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer 106 is next exposed to activating radiation 108 through a photomask 110 to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions corresponding to regions of the resist layer to be exposed and unexposed, respectively, by the activating radiation. The exposure wavelength is typically sub-400 nm, sub-300 nm or sub-200 nm such as 193 nm or an EUV wavelengths (e.g., 13.4 or 13.5 nm), with 193 nm (immersion or dry lithography) and EUV being preferred. The exposure energy is typically from about 10 to 80 mJ/cm$^2$, dependent upon the exposure tool and the components of the photosensitive composition.

Following exposure of the photoresist layer 106, a post-exposure bake (PEB) is performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds. A latent image defined by the boundary between polarity-switched and unswitched regions (corresponding to exposed and unexposed regions, respectively) is thereby formed.

Figure 1E:
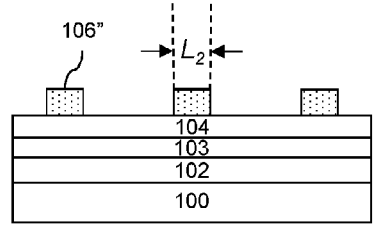
Figure 1B:
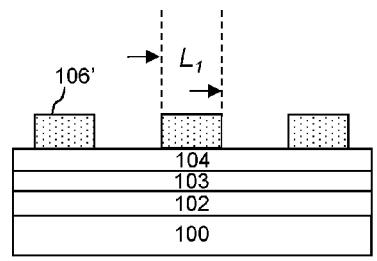

The photoresist layer 106 is next developed to remove exposed regions of the layer, leaving unexposed regions forming a resist pattern 106' having a plurality of features as shown in FIG. 1B. The features are not limited and can include, for example, a plurality of lines and/or cylindrical posts which will allow for the formation of line and/or contact hole patterns in the underlying layers to be patterned. The formed patterns have an initial dimension shown as $L_1$, a linewidth in the case of line patterns or post diameter for post patterns. In the case of a negative tone development process, where unexposed regions of the photoresist layer are removed and exposed regions remain to form the resist pattern, an organic solvent developer is employed. The organic developer can, for example, be a solvent chosen from ketones, esters, ethers, hydrocarbons, and mixtures thereof, with 2-heptanone and n-butyl acetate being typical.

Figure 1F:
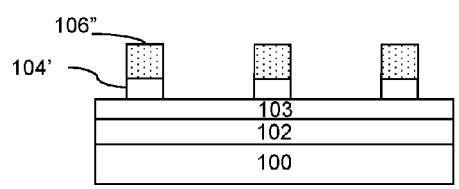
Figure 1C:
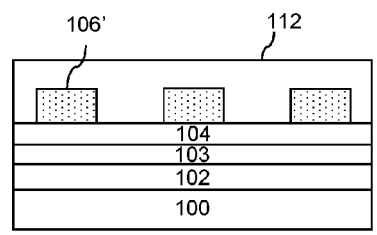

A layer 112 of a photoresist pattern trimming composition as described herein is formed over the photoresist pattern 106' as shown in FIG. 1C. The trimming composition is typically applied to the substrate by spin-coating. The solids content of the coating solution can be adjusted to provide a desired film thickness based upon the specific coating equipment utilized, the viscosity of the solution, the speed of the coating tool and the amount of time allowed for spinning. A typical thickness for the pattern trimming layer 112 is from 200 to 1500 Å.

Figure 1G:
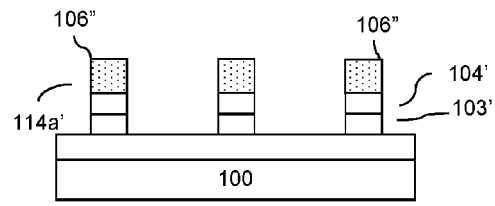
Figure 1D:
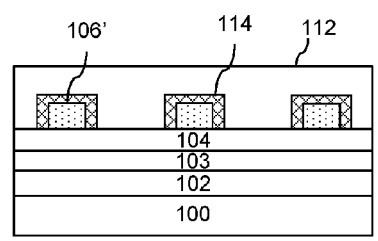

As shown in FIG. 1D, the substrate is next baked to remove solvent in the trimming layer, to allow for the free acid to diffuse into the surface of the underlying resist pattern 106' and the polarity-changing reaction in the resist pattern surface region 114. The bake can be conducted with a hotplate or oven, with a hotplate being typical. Suitable bake temperatures are greater than 50° C., for example, greater than 70° C., greater than 90° C., greater than 120° C. or greater than 150° C., with a temperature of from 70 to 160° C. and a time of from about 30 to 90 seconds being typical. While a single baking step is typical, multiple-step baking can be used and may be useful for resist profile adjustment.

The photoresist pattern is next contacted with a rinsing agent, typically a developing solution, to remove the residual trimming composition layer 112 and the surface region 114 of the photoresist pattern, with the resulting trimmed pattern 106" being shown in FIG. 1E. The rinsing agent is typically an aqueous alkaline developer, for example, a quaternary ammonium hydroxide solution, for example, a tetra-alkyl ammonium hydroxide solutions such as 0.26 Normality (N) (2.38 wt %) tetramethylammonium hydroxide (TMAH). Alternatively, an organic solvent developer can be used, for example, a solvent chosen from ketones, esters, ethers, hydrocarbons, and mixtures thereof, such as 2-heptanone and n-butyl acetate. The rinsing agent can further be or comprise water. The resulting structure is shown in FIG. 1E. The resist pattern after trimming has a dimension (L$_2$) that is smaller as compared with the feature size prior to trimming.

Figure 1H:
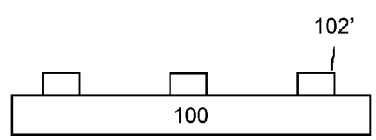

Using the resist pattern 106" as an etch mask, the BARC layer 104 is selectively etched to form BARC patterns 104', exposing the underlying hardmask layer 103, as shown in FIG. 1F. The hardmask layer is next selectively etched, again using the resist pattern as an etch mask, resulting in patterned BARC and hardmask layer 103', as shown in FIG. 1G. Suitable etching techniques and chemistries for etching the BARC layer and hardmask layer are known in the art and will depend, for example, on the particular materials of these layers. Dry-etching processes such as reactive ion etching are typical. The resist pattern 106" and patterned BARC layer 104' are next removed from the substrate using known techniques, for example, oxygen plasma ashing. Using the hardmask pattern 103' as an etch mask, the one or more layers 102 are then selectively etched. Suitable etching techniques and chemistries for etching the underlying layers 102 are known in the art, with dry-etching processes such as reactive ion etching being typical. The patterned hardmask layer 103' can next be removed from the substrate surface using known techniques, for example, a dry-etching process such as reactive ion etching or a wet strip. The resulting structure is a pattern of etched features 102' as illustrated in FIG. 1H. In an alternative exemplary method, it may be desirable to pattern the layer 102 directly using the photoresist pattern 106" without the use of a hardmask layer 103. Whether direct patterning with the resist patterns can be employed will depend on factors such as the materials involved, resist selectivity, resist pattern thickness and pattern dimensions.

The following non-limiting examples are illustrative of the invention.

EXAMPLES

Acid Synthesis

Example 1

3,5-bis((4,4,4-trifluoro-3-hydroxy-3-(trifluoromethyl)butoxy) carbonyl)benzene sulfonic acid (SIPA-DiHFA) (Acid A) was prepared according to the reaction sequence shown below in Scheme 1.

Scheme 1: Synthesis of Acid A (SIPA-DiHFA)

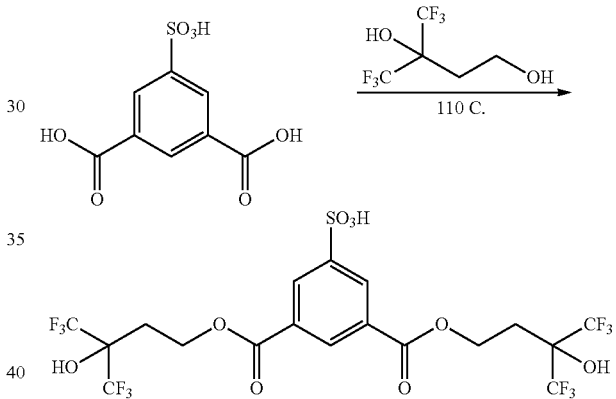

5-Sulfoisophthalic acid (6.3 g, 24.3 mmol) as a 50 wt % water solution was mixed with 15 g (70.7 mmol) of 4,4,4-trifluoro-3-(trifluoromethyl)butane-1,3-diol at room temperature, under nitrogen flow. The temperature of the reaction mixture was then raised to 110-120° C. At this temperature, the reaction was carried out for 2-3 hours with constant evaporation of water as a side product. The reaction mixture was then poured into a 1M HCl aqueous solution. After 5-10 minutes, the mixture separated into two layers. The organic layer was recovered, washed three times with 1M HCl aqueous solution, and then extracted with diethyl ether. The crude product was then dried over MgSO$_4$. The volatile contaminants were removed by rotary evaporation. The crude product was further washed with heptanes:acetone (8:2) to yield solid acid A in 64% yield. $^1$H NMR ((CD$_3$)$_2$CO, 500 MHz): δ 2.63 (t, 4H), 4.68 (t, 4H), 7.11 (bs, 3H), 8.68 (m, 3H).

Photoresist Composition Preparation

Example 2

The following monomers M1-M5 were used to form polymers for preparation of the photoresist (Photoresist Composition A) described below:

M1
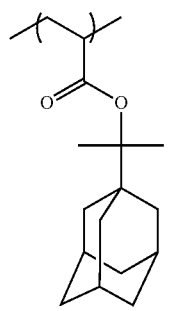

M2
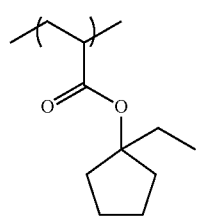

M3
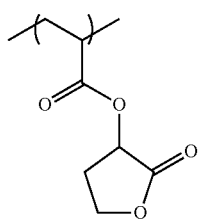

M4
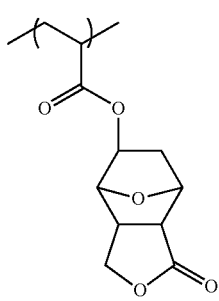

M5
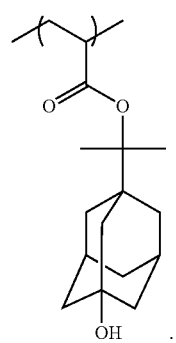

A positive chemically amplified photoresist composition was prepared by combining 4.54 g Polymer A (M1/M2/M3/M4/M5=2/1/4/1/2 mole ratio, MW=10K), 0.401 g of (4-t-butylphenyl)tetramethylene sulfonium norbornyl perfluoroethoxyethylsulfonate (TBPTMS-NBPFEES), 0.178 g triphenylsulfonium 4,4,5,5,6,6-hexafluorodihydro-4H-1,3,2-dithiazine 1,1,3,3-tetraoxide (TPS-PFSI-CY6), 0.039 g of 1-(tertbutyoxycarbonyl)-4-hydroxypiperidine (TBOC-4HP), 0.008 g of POLYFOX 656 surfactant (Omnova Solutions Inc.), 75.87 g propylene glycol methyl ether acetate and 18.97 g cyclohexanone.

Photoresist Patterned Wafer Preparation 8-inch silicon wafers coated with an 80 nm BARC layer (AR™40A antireflectant, Dow Electronic Materials, Marlborough, Mass. USA) were spin-coated with Photoresist Composition A and softbaked at 100° C. for 60 seconds to provide a resist layer thickness of 900 Å. The wafers were exposed using an ASML ArF 1100 scanner with NA=0.75, Dipole 35Y illumination (0.89/0.64sigma), using a mask having line and space patterns with PSM feature size of 120 nm 1:1, under dipole-35Y with outer/inner sigma of 0.89/0.64. The exposed wafers were post-exposure baked at 100° C. for 60 seconds and developed with a 0.26N TMAH solution to form a 120 nm 1:1 line and space pattern (duty ratio=1:1) imaged resist layer. CDs for the patterns were determined by processing the image captured by top-down scanning electron microscopy (SEM) using a Hitachi 9380 CD-SEM, operating at an accelerating voltage of 500 volts (V), probe current of 5.0 picoamperes (pA), using 150 Kx magnification. Three exposure latitudes were taken for each wafer and averaged. The averaged exposure latitude was then fit using a polynomial regression to determine the correct sizing dose of the 120 nm lines for the case of no resist pattern trimming. This sizing dose was then used with the polynomial regression of the resist pattern-trimmed wafers to calculate the final CD of each pattern-trimmed wafer. The results of the CD measurements are shown in Table 1.

Photoresist Trimming Compositions, Pattern Trimming and Evaluation

Example 3

(Comparative) (PTC-1)

0.628 g copolymer of n-butylmethacrylate/methacrylic acid polymer (77/23 weight ratio), 0.02 g p-toluene sulfonic acid (PTSA), 23.48 g methyl isobutyl carbinol and 5.87 g isoamyl ether were mixed until all components dissolved. The mixture was filtered with a 0.2 micron Nylon filter, resulting in photoresist trimming composition PTC-1. A 60 nm film of PTC-1 was spin-coated on a photoresist-coated wafer of Example 3, baked at 70° C. for 120 seconds on a hotplate and developed in 2.38 wt % TMAH developer for 12 seconds with an SH nozzle. CDs of the trimmed patterns were measured in the same manner as the pre-trimmed patterns, with the results shown in Table 1.

Example 4

PTC-2

0.579 g copolymer of n-butylmethacrylate/methacrylic acid polymer (77/23 weight ratio), 0.069 g Acid A (SIPA-DiHFA), 12.007 g methyl isobutyl carbinol and 5.87 g isoamyl ether were mixed until all components dissolved. The content of Acid A in PCT-2 is equimolar to the PTSA content in Example 3. The mixture was filtered with a 0.2 micron Nylon filter, resulting in photoresist trimming composition PTC-2. A 60 nm film of PTC-3 was spin-coated on a photoresist-coated wafer of Example 3, baked at respective temperatures of 70° C., 80° C., 90° C. and 100° C. for 60 seconds on a hotplate, and developed in 2.38 wt % TMAH developer for 12 seconds with an SH nozzle. CDs of the trimmed patterns were measured in the same manner as the pre-trimmed patterns, with the results shown in Table 1.

TABLE 1

| Example | Trim Composition | Acid | Bake Temp (° C.) | Final CD (nm) | ΔCD (nm) |
|---|---|---|---|---|---|
| before trim | — | — | — | 119.94 | 0 |
| 3 (Comp) | PTC-1 | PTSA | 70 | 97.55 | 22.39 |
| 4 | PTC-2 | SIPA-DiHFA | 70 | 109.58 | 10.36 |
|  |  |  | 80 | 106.39 | 13.55 |
|  |  |  | 90 | 103.5 | 16.44 |
|  |  |  | 100 | 97.05 | 22.89 |

Resist pattern trimming composition PTC-2 which contains bulky acid SIPA-DiHFA groups at equimolar loading resulted in significant pattern trimming, but less than the p-toluenesulfonic acid of Comparative Example 3. The amount of pattern trim increased with increases in bake temperature from 70 to 100° C., indicative of slow diffusion of the acid in the resist.

LWR values for the patterns were determined by processing the image captured by top-down SEM using the tool and conditions described above. Local LWR was measured at 20 points in five different locations on the wafer and the measurements were averaged to calculate the LWR. CDs for the 1:1 and 1:8 patterns were determined by processing the SEM images.

Iso-dense bias was calculated based on the pre- and post-trimming CD measurements using the following equation:

$$IDB = \Delta CD_{1:8} - \Delta CD_{1:1}$$

wherein: IDB=iso-dense bias; $\Delta CD_{1:8}$=[(CD of the 120 nm 1:8 pattern before trimming)−(CD of the 120 nm 1:8 pattern after trimming)]; and $\Delta CD_{1:1}$=[(CD of the 120 nm 1:1 pattern before trimming)−(CD of the 120 nm 1:1 pattern after trimming)]. Iso-dense bias provides an indication of whether an existing photomask can be used to print isolated and dense patterns on the mask without the need for Optical Proximity Correction (OPC). If OPC is required, a new photomask is typically required. An iso-dense bias of 10 nm or more was considered poor and less than 10 nm was considered good. The results for CD, LWR and iso-dense bias are provided in Table 2.

TABLE 2

| Example | Bake Temperature (° C.) | Trim Composition | Acid | ΔCD (nm) | LWR (nm) | Iso-Dense Bias (nm) |
|---|---|---|---|---|---|---|
| before trim | — | — | — | 0 | 9.0 | 0 |
| 3 (Comp) | 70 | PTC-1 | PTSA | 22.39 | 6.8 | 6.02 |
| 4 | 90 | PTC-2 | SIPA-DiHFA | 16.44 | 7.2 | 3.3 |

The results shown in Table 2 indicate that the photoresist patterns were effectively reduced in CD by trimming composition PTC-2. LWR was significantly improved as compared with the pre-trimmed resist pattern. While different bake temperatures were used for Examples 3 and 4, it is expected that an increase in bake temperature to 90° C. for Example 3 would result in worsening of LWR and iso-dense bias, and an increase in ΔCD. With that assumption, the results indicate a significant improvement in iso-dense bias for trimming composition PTC-2 in accordance with the invention as compared with the trimming composition of Comparative Example 3.

What is claimed is:

1. A photoresist pattern trimming composition, comprising: a matrix polymer, an aromatic sulfonic acid and a solvent, wherein the aromatic sulfonic acid comprises one or more fluorinated alcohol group.

2. The photoresist pattern trimming composition of claim 1, wherein the fluorinated alcohol group comprises a fluorine atom bonded to a carbon at the alpha position of the alcohol hydroxyl.

3. The photoresist pattern trimming composition of claim 1, wherein the fluorinated alcohol group comprises a fluorinated group bonded pendant to a carbon at the alpha position of the alcohol hydroxyl.

4. The photoresist pattern trimming composition of claim 1, wherein the aromatic sulfonic acid comprises a hexafluoroalcohol group.

5. The photoresist pattern trimming composition of claim 1, wherein the aromatic sulfonic acid comprises a plurality of fluorinated alcohol groups.

6. The photoresist pattern trimming composition of claim 1, wherein the fluorinated alcohol group is bonded to an aromatic ring of the aromatic sulfonic acid through an ester group.

7. The photoresist pattern trimming composition of claim 1, wherein the aromatic sulfonic acid is chosen from the following acids:

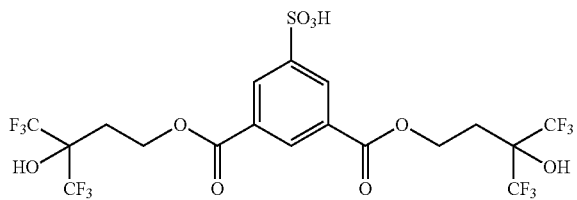

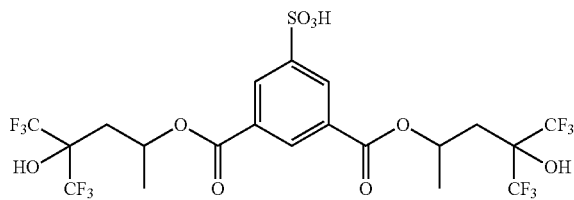

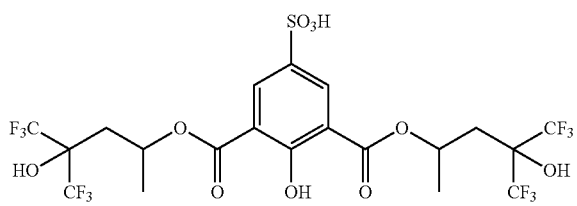

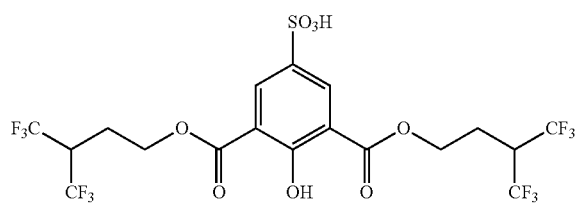

-continued
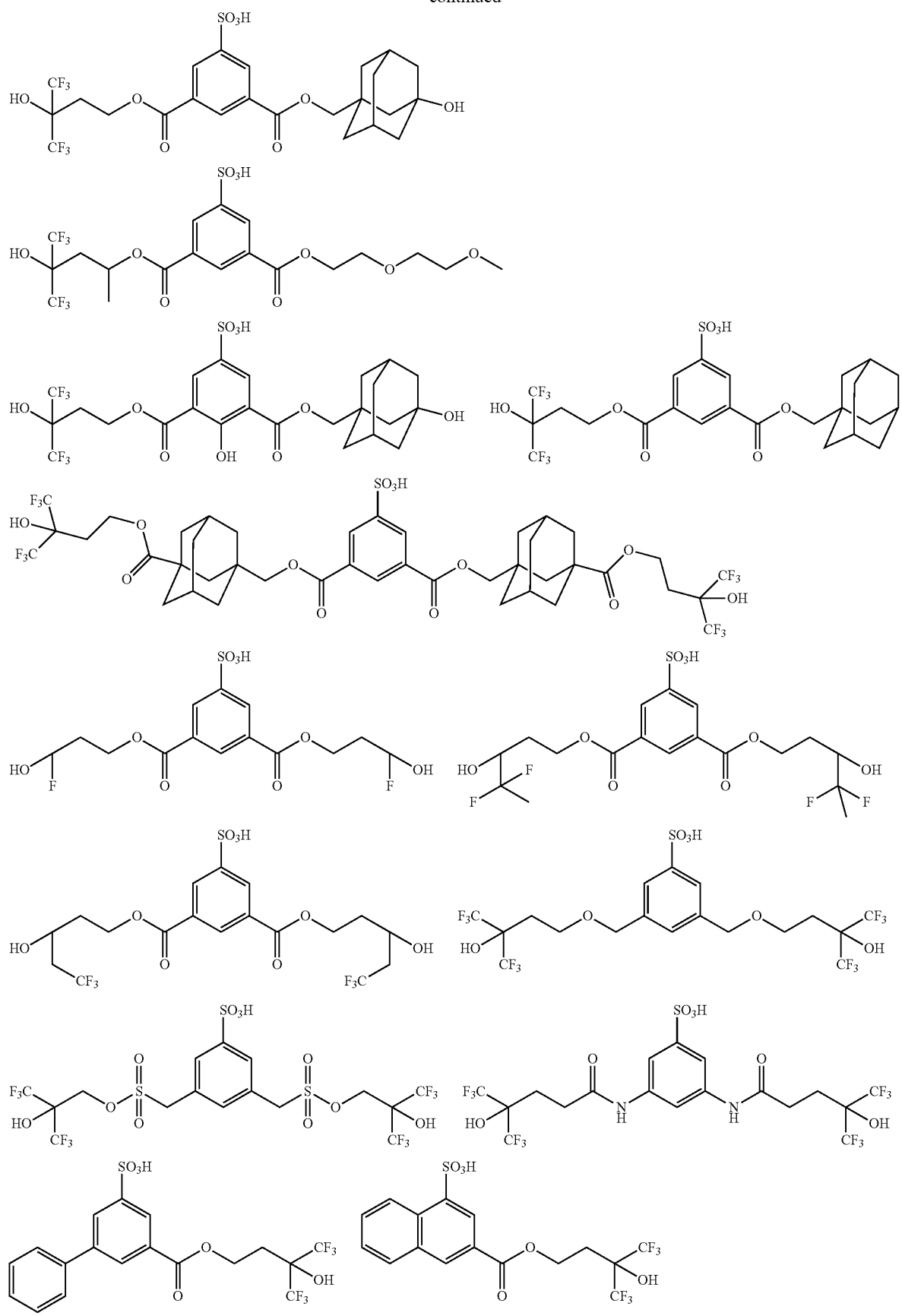

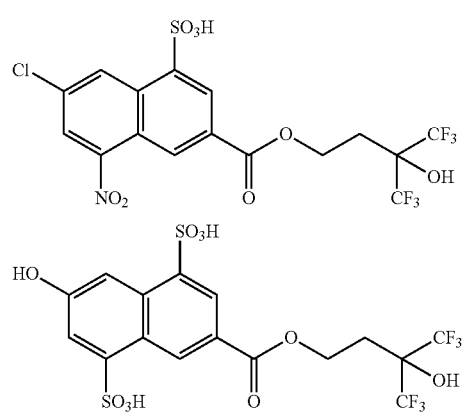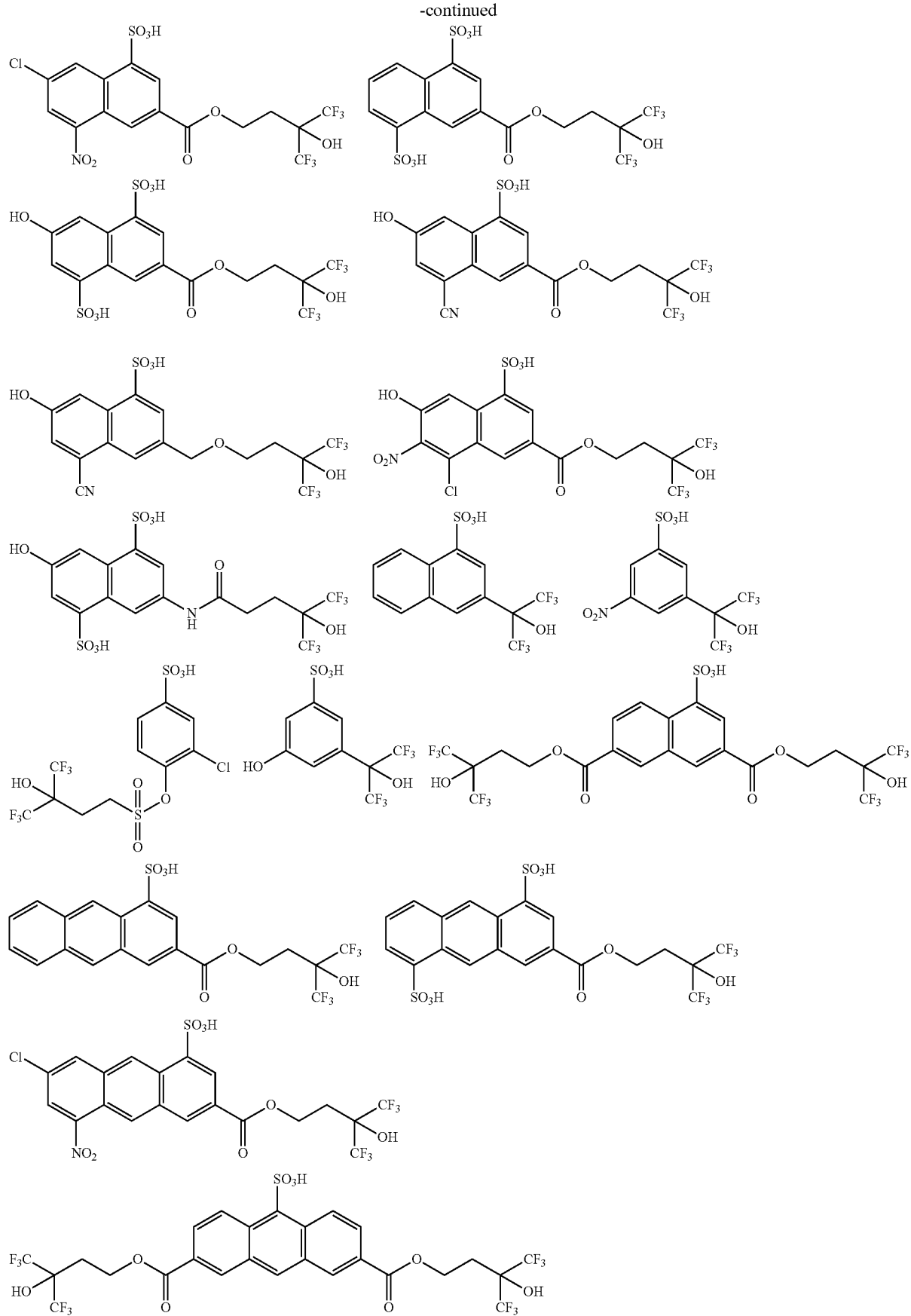

27 28
-continued
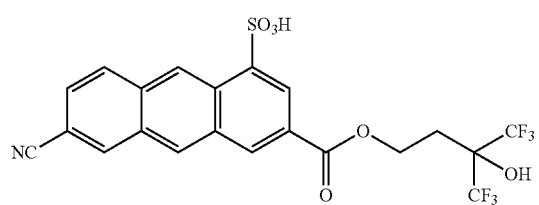
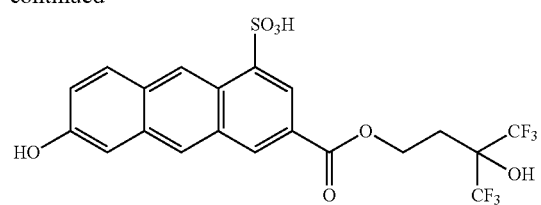
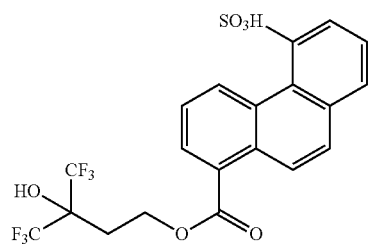
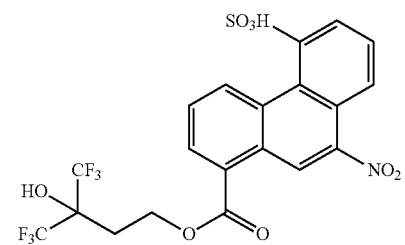
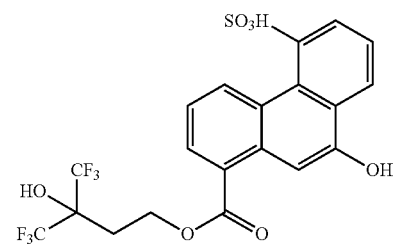
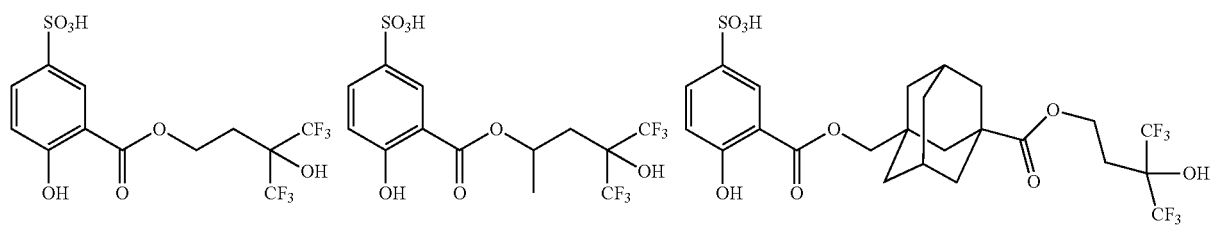
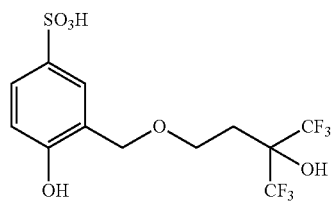
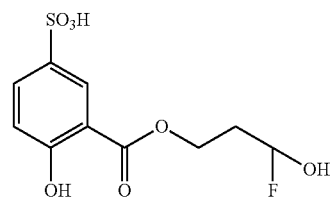
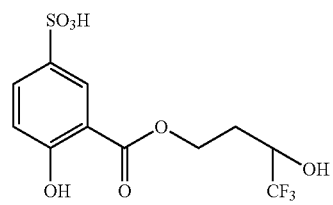
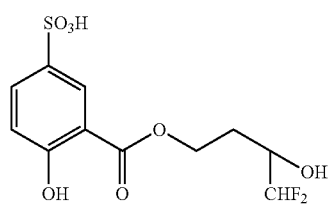
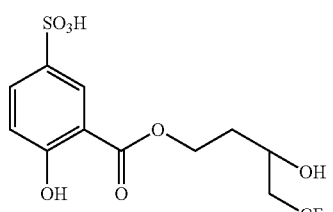
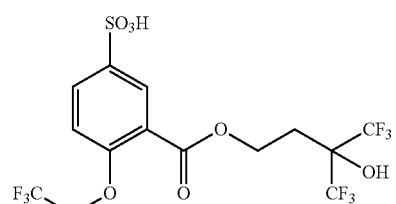
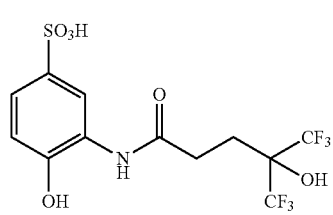
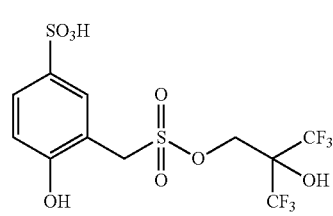
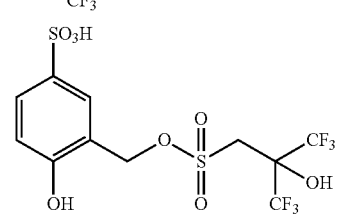
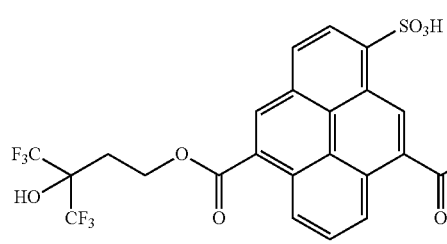
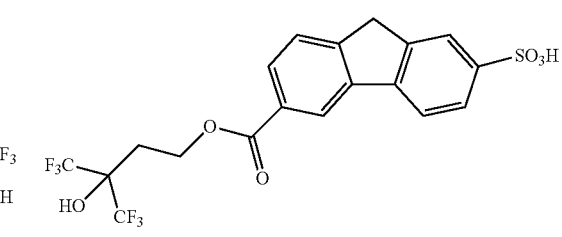

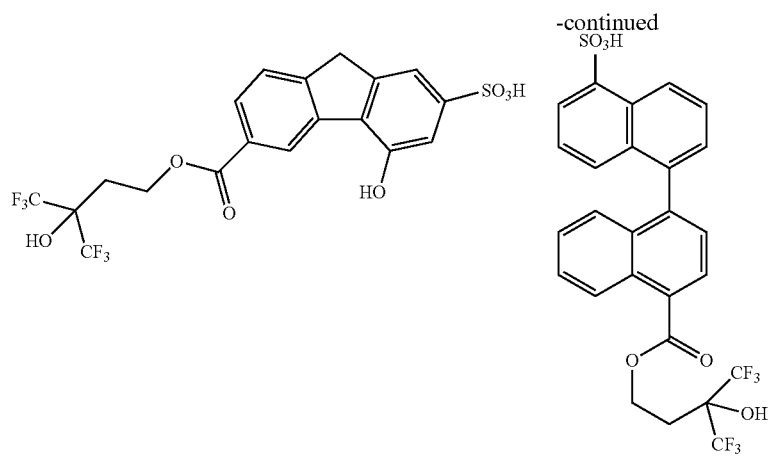

-continued

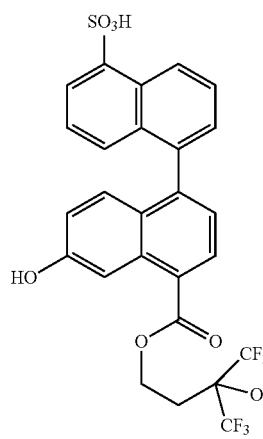

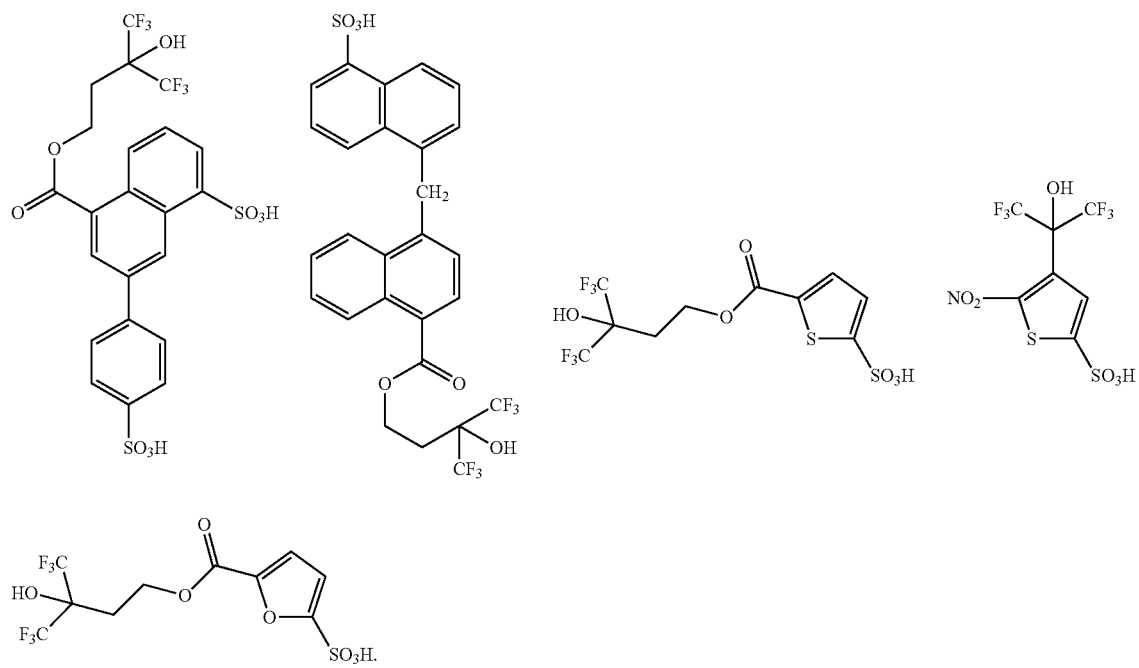

8. The photoresist pattern trimming composition of claim 1, wherein the matrix polymer is a poly(meth)acrylate polymer.

9. A method of trimming a photoresist pattern, comprising:
(a) providing a semiconductor substrate;
(b) forming a photoresist pattern on the substrate, wherein the photoresist pattern is formed from a photoresist composition comprising: a matrix polymer comprising an acid labile group, a photoacid generator, and a solvent;
(c) coating a photoresist trimming composition of claim 1 on the substrate over the photoresist pattern;
(d) heating the coated substrate, thereby causing a change in polarity of the photoresist matrix polymer in a surface region of the photoresist pattern; and
(e) contacting the photoresist pattern with a rinsing agent to remove the surface region of the photoresist pattern, thereby forming a trimmed photoresist pattern.

10. The method of claim 9, wherein the photoresist pattern is formed in an immersion lithography process.

11. The method of claim 9, wherein the fluorinated alcohol group comprises a fluorine atom bonded to a carbon at the alpha position of the alcohol hydroxyl.

12. The method of claim 9, wherein the fluorinated alcohol group comprises a fluorinated group bonded pendant to a carbon at the alpha position of the alcohol hydroxyl.

13. The method of claim 9, wherein the aromatic sulfonic acid comprises a hexafluoroalcohol group.

14. The method of claim 9, wherein the aromatic sulfonic acid comprises a plurality of fluorinated alcohol groups.

15. The method of claim 9, wherein the fluorinated alcohol group is bonded to an aromatic ring of the aromatic sulfonic acid through an ester group.

16. The method of claim 9, wherein the aromatic sulfonic acid is chosen from the following acids:

31                          32
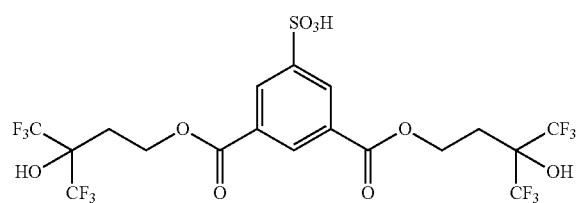
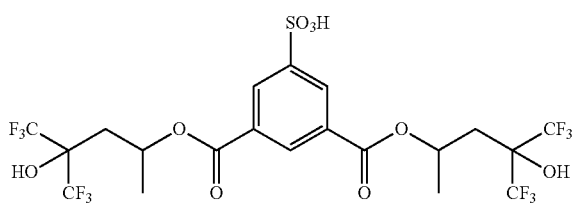
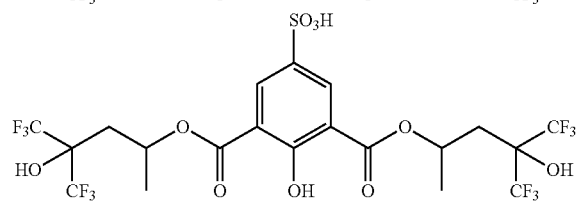
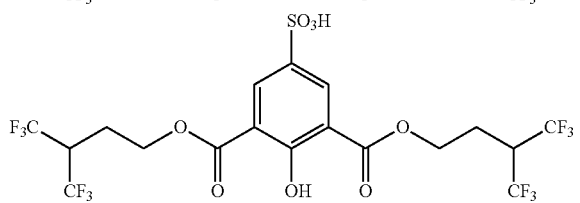
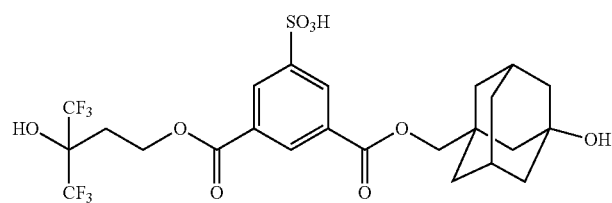
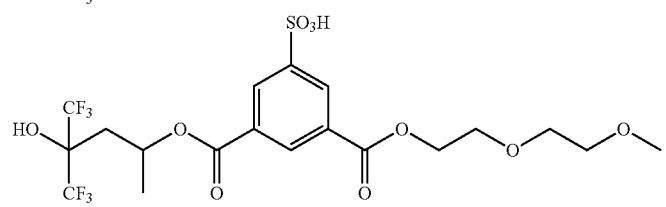
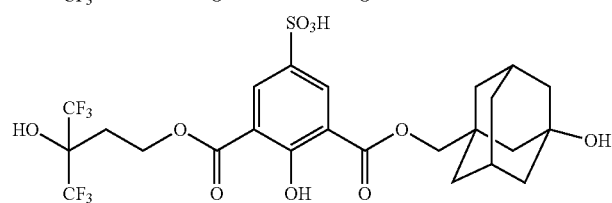
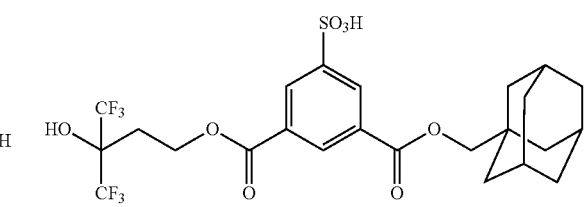
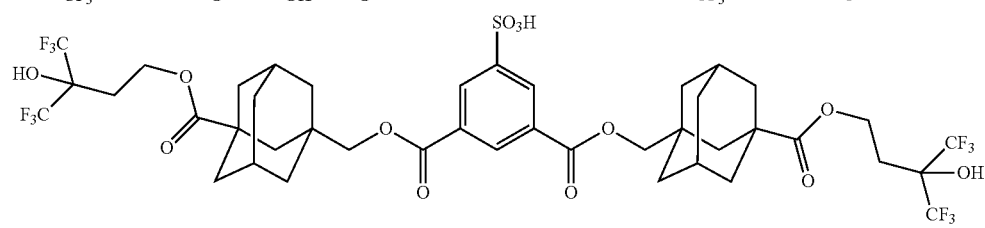
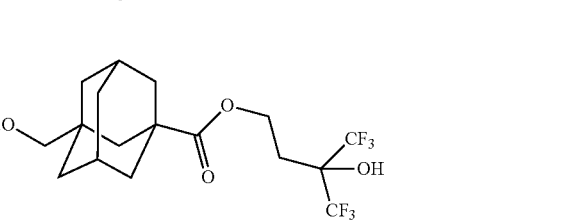
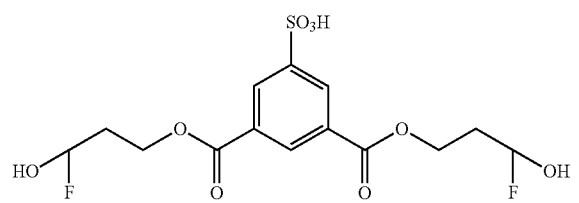
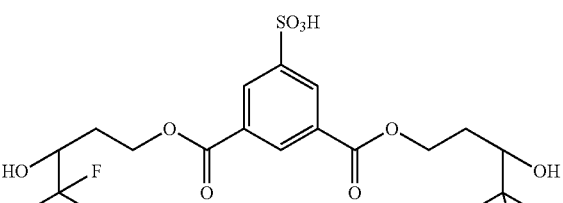
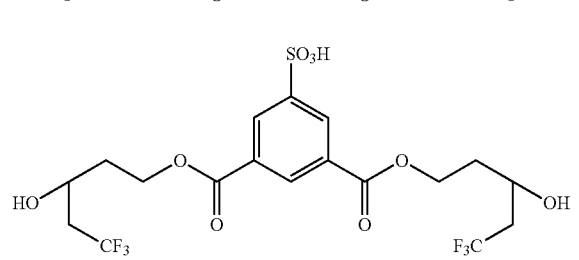
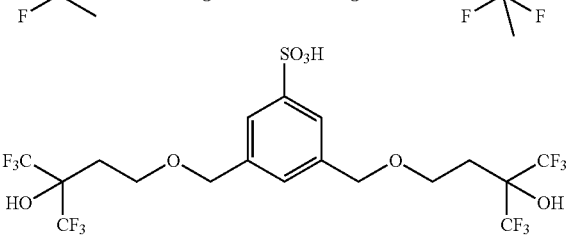

-continued
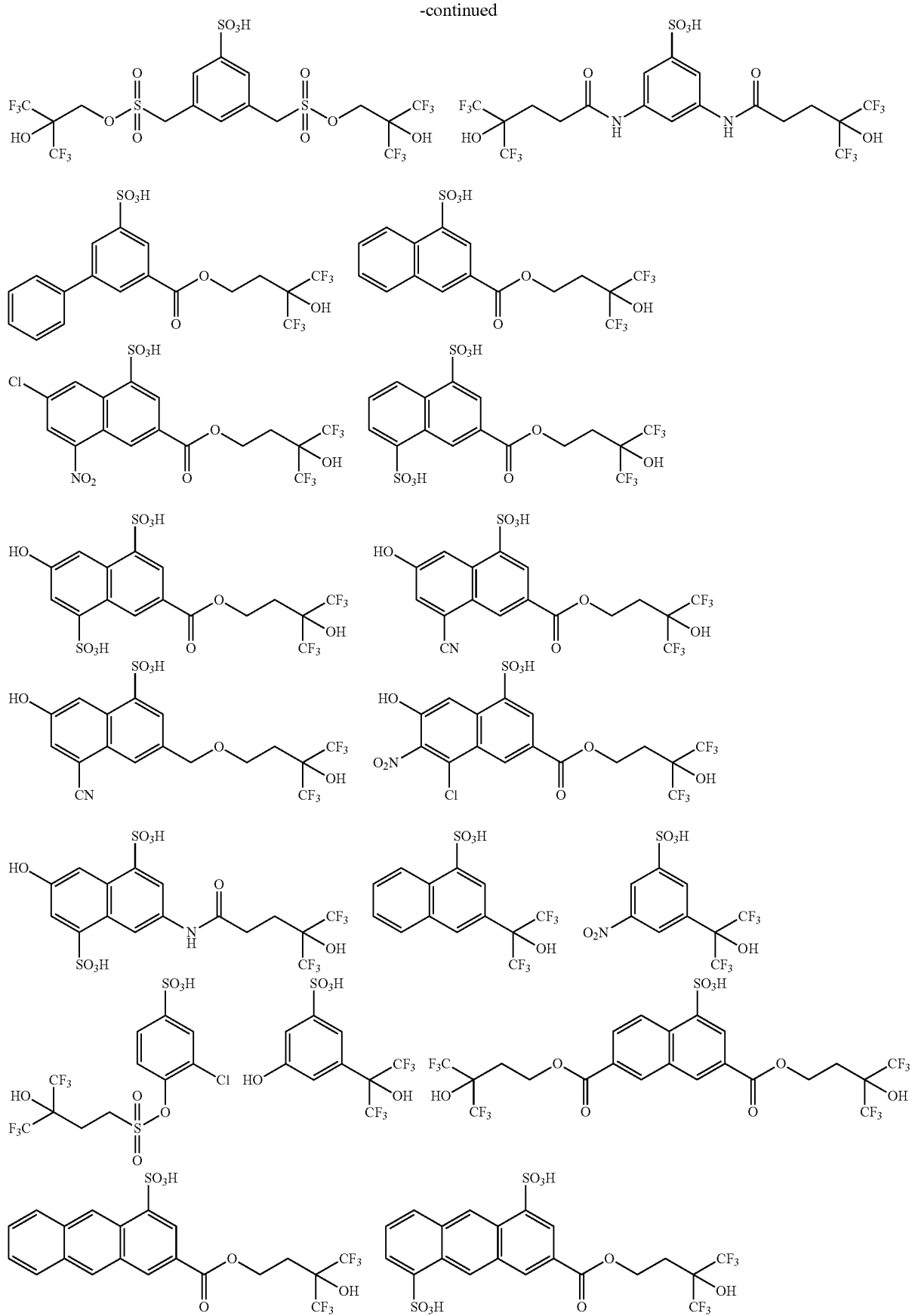

-continued
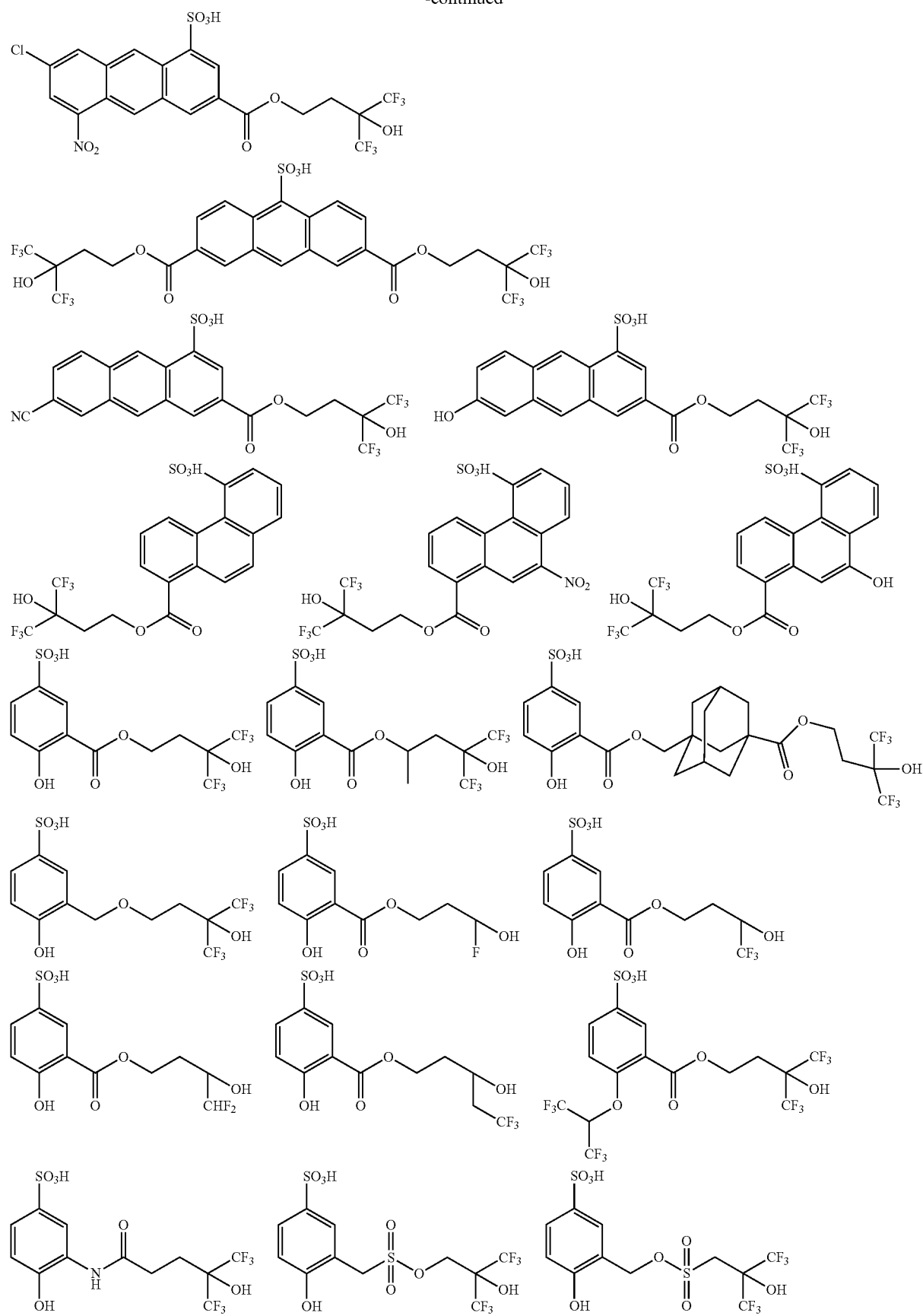

-continued

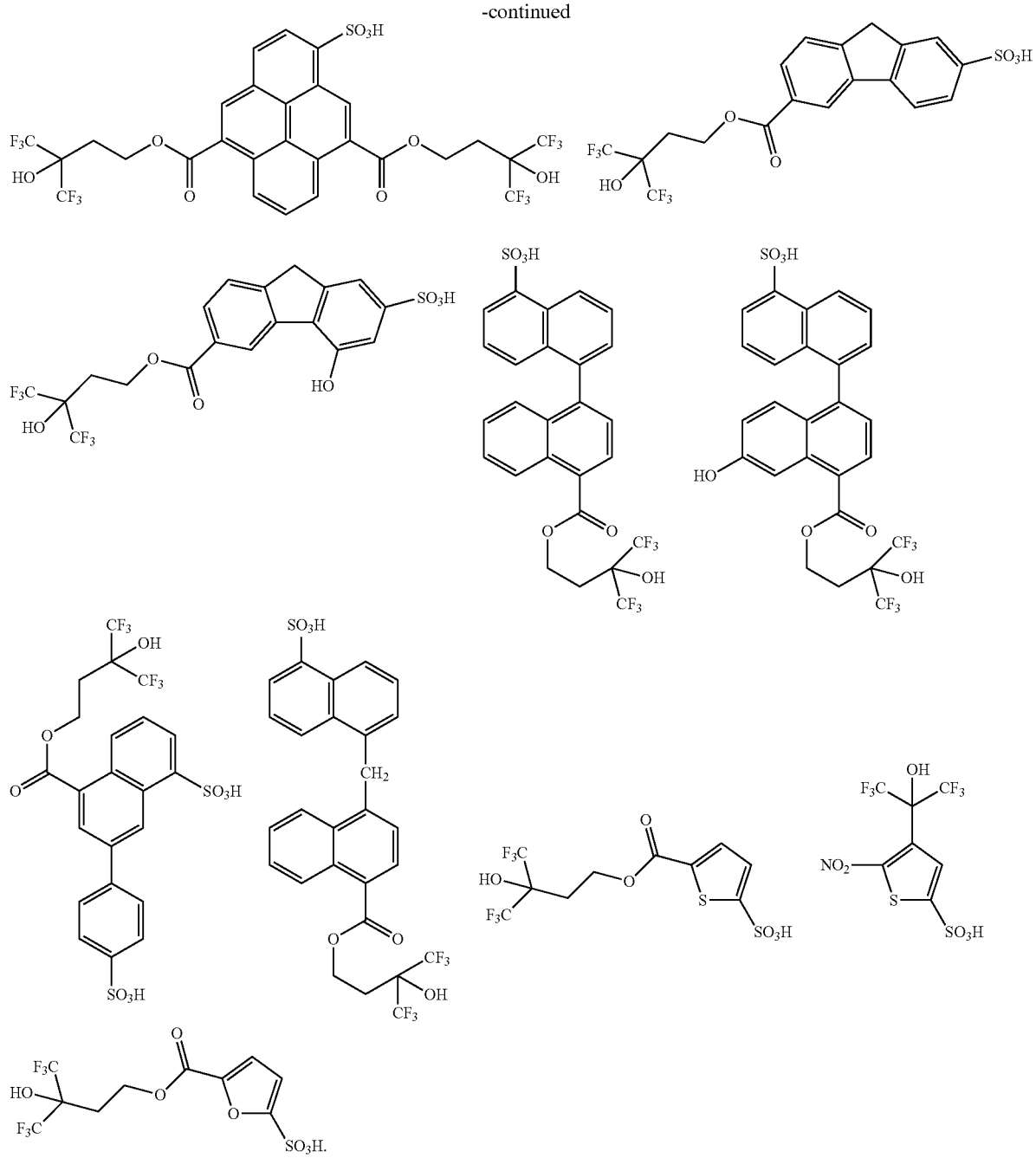

17. The method of claim 9, wherein the matrix polymer is a poly(meth)acrylate polymer.

18. The photoresist pattern trimming composition of claim 1, wherein the aromatic sulfonic acid is represented by the following general formula (I):

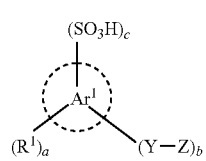

wherein $Ar^1$ represents an optionally substituted aromatic group; $R^1$ independently represents a group chosen from carboxyl, hydroxy, nitro, cyano, C1-5 alkoxy and formyl; Y independently represents a linking group; Z independently represents a group chosen from fluorinated alcohols, fluorinated esters, substituted or unsubstituted alkyl, C5 or higher monocyclic, polycyclic, fused polycyclic cycloaliphatic, or aryl, which may optionally comprise a heteroatom, provided at least one occurrence of Z is a fluorinated alcohol group; a is an integer of 0 or greater; b is an integer of 1 or greater; c is an integer of 1 or greater; and a+ b+ c is at least 2 and not greater than the total number of available aromatic carbon atoms of $Ar^1$.

19. The photoresist pattern trimming composition of claim 1, wherein the aromatic acid is present in an amount of from 0.01 to 20 wt% based on total solids of the trimming composition.

20. The method of claim 9, wherein the aromatic sulfonic acid is represented by the following general formula (I):

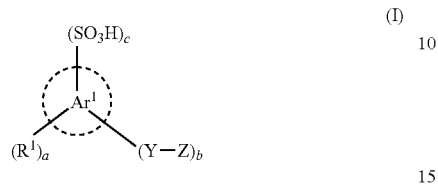

wherein $Ar^3$ represents an optionally substituted aromatic group; $R^1$ independently represents a group chosen from carboxyl, hydroxy, nitro, cyano, C1-5 alkoxy and formyl; Y independently represents a linking group; Z independently represents a group chosen from fluorinated alcohols, fluorinated esters, substituted or unsubstituted alkyl, C5 or higher monocyclic, polycyclic, fused polycyclic cycloaliphatic, or aryl, which may optionally comprise a heteroatom, provided at least one occurrence of Z is a fluorinated alcohol group; a is an integer of 0 or greater; b is an integer of 1 or greater; c is an integer of 1 or greater; and a+ b+ c is at least 2 and not greater than the total number of available aromatic carbon atoms of $Ar^1$.

21. The method of claim 9, wherein the aromatic acid is present in an amount of from 0.01 to 20 wt% based on total solids of the trimming composition.

* * * * *